(12) United States Patent
Taha et al.

(10) Patent No.: US 10,105,513 B2
(45) Date of Patent: Oct. 23, 2018

(54) SECURED AND SELF CONTAINED SPINAL CORD STIMULATOR LEADS AND CATHETERS

(71) Applicant: SPINELOOP, LLC, Newport Beach, CA (US)

(72) Inventors: Ashraf Taha, Irvine, CA (US); Abdullah Kaki, Jeddah (SA); John Koelsch, Capistrano Beach, CA (US)

(73) Assignee: SPINELOOP, LLC, Newport Beach, CA (US)

( * ) Notice: Subject to any disclaimer, the term of this patent is extended or adjusted under 35 U.S.C. 154(b) by 544 days.

(21) Appl. No.: 14/494,906

(22) Filed: Sep. 24, 2014

(65) Prior Publication Data

US 2015/0174366 A1    Jun. 25, 2015

Related U.S. Application Data

(60) Provisional application No. 62/017,156, filed on Jun. 25, 2014, provisional application No. 61/881,924, filed on Sep. 24, 2013.

(51) Int. Cl.

| | | |
|---|---|---|
| *A61M 25/00* | (2006.01) | |
| *A61N 1/05* | (2006.01) | |
| *A61N 1/36* | (2006.01) | |
| *A61M 5/14* | (2006.01) | |

(52) U.S. Cl.
CPC .......... *A61M 25/0043* (2013.01); *A61M 5/14* (2013.01); *A61N 1/0553* (2013.01); *A61N 1/0558* (2013.01); *A61N 1/36071* (2013.01); *A61M 2025/0007* (2013.01); *A61M 2025/0057* (2013.01)

(58) Field of Classification Search
CPC ... A61M 25/0043; A61M 5/14; A61N 1/0553; A61N 1/36071
USPC ..................................... 607/46, 117; 606/41
See application file for complete search history.

(56) References Cited

U.S. PATENT DOCUMENTS

| | | | |
|---|---|---|---|
| 4,538,624 A | | 9/1985 | Tarjan |
| 6,141,594 A | * | 10/2000 | Flynn .................... A61N 1/056 600/374 |
| 7,203,548 B2 | * | 4/2007 | Whitehurst .......... A61N 1/0556 607/118 |

(Continued)

FOREIGN PATENT DOCUMENTS

EP    1181947 A2    2/2002

OTHER PUBLICATIONS

International Search Report and Written Opinion dated Jan. 9, 2015, from corresponding PCT application No. PCT/US2014/057217.

*Primary Examiner* — Christopher D Koharski
*Assistant Examiner* — Roland Dinga
(74) *Attorney, Agent, or Firm* — One LLP

(57) ABSTRACT

A stimulator lead is herein disclosed. The stimulator lead includes a proximal portion that is configured for placement external the epidural space through a first opening, wherein said proximal portion is operatively connected to an IPG unit, a distal portion that is configured for placement external the epidural space through a second opening, and a third portion between the proximal and distal portions that is configured for percutaneous placement in an epidural space, wherein said middle portion includes at least one stimulator electrode for placement adjacent to target dura.

9 Claims, 9 Drawing Sheets

(56) References Cited

U.S. PATENT DOCUMENTS

| | | | |
|---|---|---|---|
| 7,254,445 B2 * | 8/2007 | Law | A61N 1/36071 607/2 |
| 7,945,331 B2 * | 5/2011 | Vilims | A61M 5/14276 607/117 |
| 2005/0246006 A1 * | 11/2005 | Daniels | A61N 1/0551 607/117 |
| 2011/0166621 A1 * | 7/2011 | Cowan | A61N 1/37217 607/46 |
| 2012/0059446 A1 * | 3/2012 | Wallace | A61N 1/0553 607/117 |
| 2012/0215218 A1 * | 8/2012 | Lipani | A61B 18/1492 606/41 |
| 2013/0023880 A1 * | 1/2013 | Tramboo | A61B 17/149 606/79 |

* cited by examiner

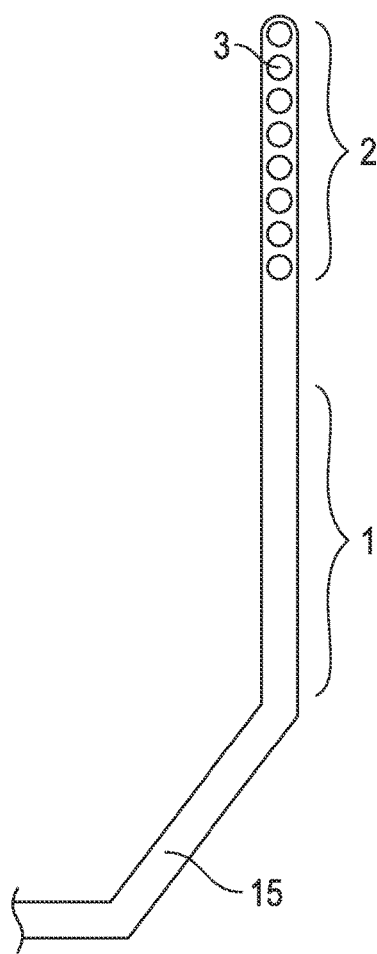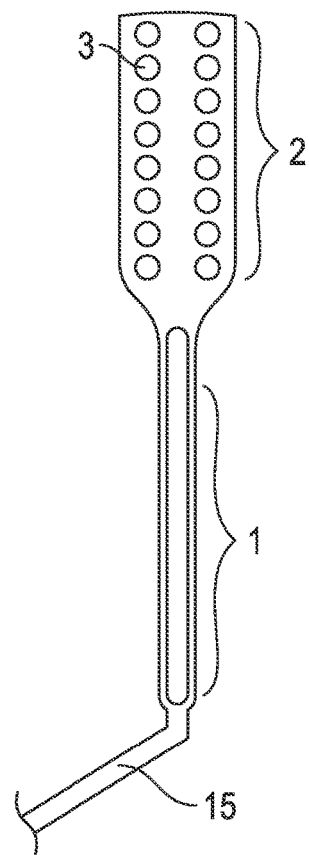
FIG. 1
(Prior Art)
FIG. 2
(Prior Art)

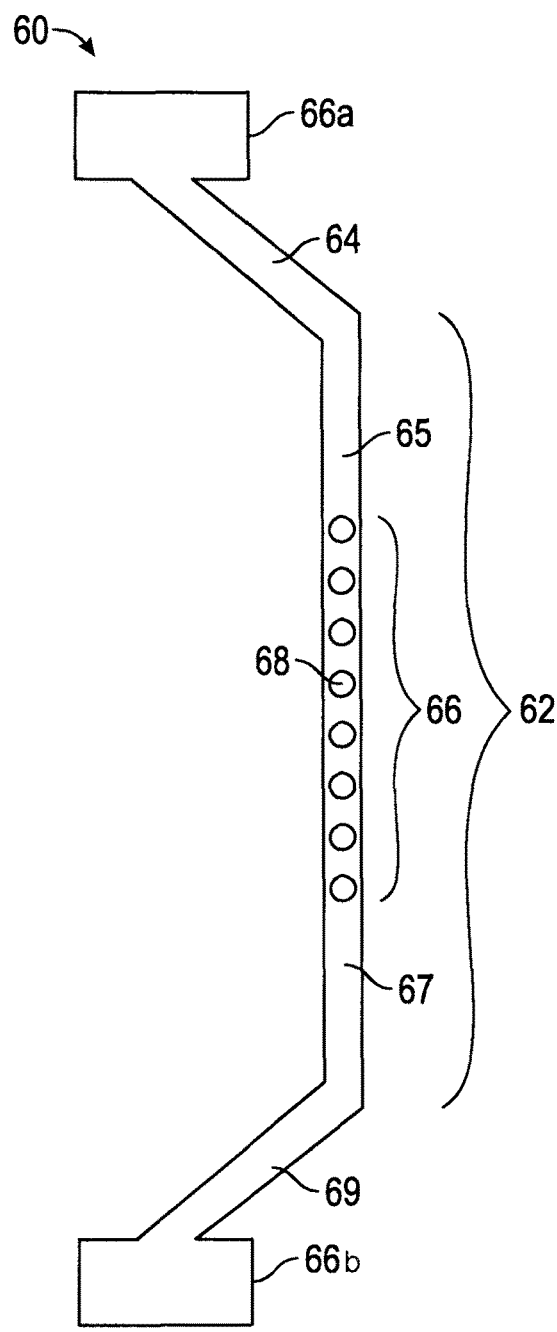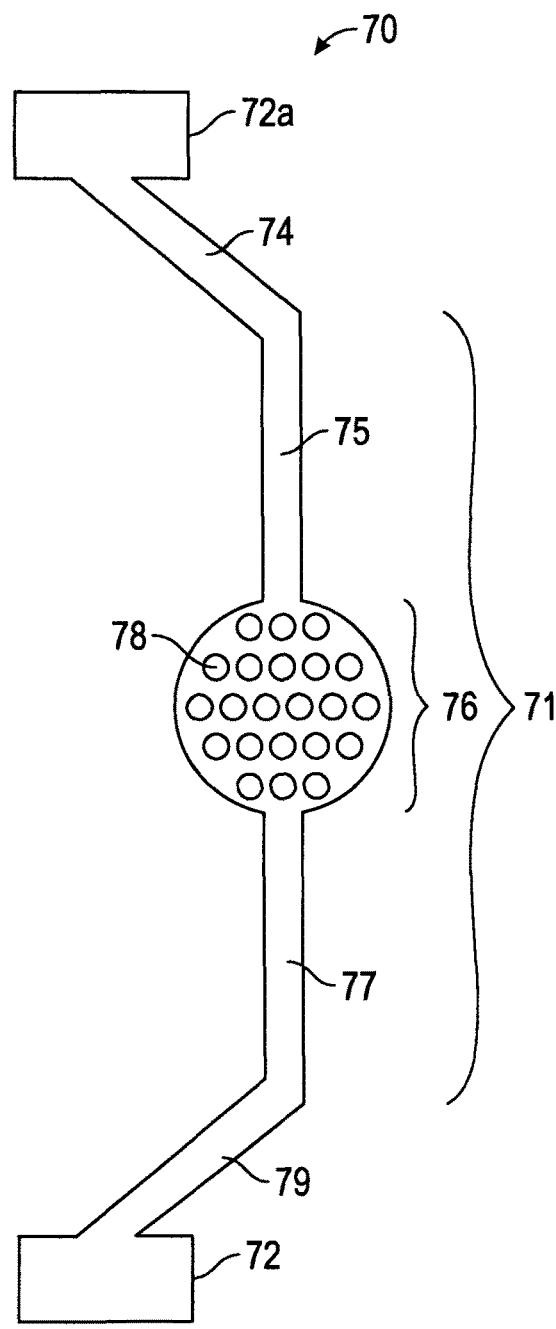
FIG. 6
FIG. 7

SECURED AND SELF CONTAINED SPINAL CORD STIMULATOR LEADS AND CATHETERS

CROSS REFERENCE TO RELATED APPLICATIONS

This application claims the benefit of U.S. Provisional Application Nos. 61/881,924, filed Sep. 24, 2013, and 62/017,156, filed Jun. 25, 2014.

BACKGROUND OF THE INVENTION

Technical Field

The disclosed technology relates generally to medical devices, and more particularly, some embodiments relate to neuromodulation and implantable medical devices that provide proximal and distal stability to a stimulator lead, pain pump, and/or other similar medical devices that may be placed in the epidural space.

Description of the Related Art

Spinal stimulation has been in practice as a means of pain control for patients after the gate theory was proposed in 1965 by Melzack and Wall. Spinal cord stimulation through implantable means was performed by Shealy et al. for the treatment of chronic pain where the first spinal cord stimulator was placed within the dorsal column for treatment of chronic pain shortly after the discovery of Melzack and Wall.

Traditionally, a spinal cord stimulation lead typically comes in two types of leads. The first, is a wire-like lead with leads that are placed at the end of the wire, i.e., the distal end. A second type of spinal cord stimulator lead is a surgical lead or a paddle lead that typically has a wider area of stimulation. This second type of spinal cord stimulator lead is generally inserted under surgical technique and may require partial laminotomy to be performed (also known as a paddle lead), and also has its stimulation portion or site at the distal end of the wire or paddle where the first part of the leads would be considered the proximal end.

In providing analgesic relief to patients with pain, spinal cord stimulator leads may provide electrical stimulation using an electric pulse generator that may be connected to conducting wires that subsequently connect or reach the distal portion of the wire where either the leads of the wire or the leads of the paddle are located. Thus, when stimulated, the leads adjacent to the spinal cord dura would provide stimulation that will help alleviate pain. With either percutaneous or surgically implanted stimulator leads, the current practice allows control from only the proximal end of the stimulator leads. This makes it very difficult for the practitioner to accurately position the stimulator lead in the correct location in the epidural space in order to provide appropriate pain relief. Insertion of the stimulator lead may traverse many levels of the spine and the only control to date is from the proximal end (end closest to practitioner from where it is inserted in the body). In standard practice today, conventional stimulator leads have no control mechanism where the practitioner may control the distal end of the lead (the portion furthest away from the point of entry of the body as well as the practitioner). Having only one entry point and one point of control makes not only navigation difficult for spinal cord stimulation, but also leads to other issues such as lead migration and lead retrieval issues if the leads break while inside the body.

BRIEF SUMMARY OF THE INVENTION

The technology disclosed herein relates to a neuromodulation and implantable medical device that provides distal and proximal stability to a spinal cord stimulator lead that may be placed in the epidural space of the spine by percutaneous techniques thereby eliminating some of the most common causes of spinal cord treatment failure. There are a plurality of different exemplary models herein disclosed, each embodiment directed at a different innovative concept. By way of example, one embodiment may have a distal and a proximal end exiting the spinal cord and patient's body, wherein the middle portion of the stimulator lead is placed within the epidural space of the spine laying adjacent the targeted area of the dura or exiting nerves of the spinal cord. In this embodiment, the practitioner may secure the proximal and distal ends outside the epidural space and thus firmly control the placement of the middle portion of the dual input, dual source (DIDS) spinal cord stimulator lead.

The DIDS spinal cord stimulator lead may be placed into an epidural space using a percutaneous technique where it may be placed at any level of the spinal cord. It may be utilized to relieve, for example, chronic pain, radiculopathies, intractable pain and so forth. The DIDS spinal cord stimulator lead may also be configured to reduce or even eliminate lead migration seen in most conventional stimulators leads. This can be accomplished, for example, by securing its two ends (proximal and distal) outside the epidural space where the middle portion of the dual source dual input spinal cord DIDS stimulator lead may not move out of place; effectively eliminating lead migration issues as compared to conventional stimulator leads.

One aspect of an example spinal cord stimulator lead is disclosed. In some embodiments, a spinal cord stimulator includes a proximal portion that is configured for placement external the human anatomy through a first opening, wherein said proximal portion is operatively connected to an IPG unit, a distal portion that is configured for placement external the human anatomy through a second opening, and a middle portion that is configured for percutaneous placement in an epidural space, wherein said middle portion includes at least one stimulator electrode for placement adjacent to target dura.

One aspect of the DIDS spinal cord stimulator lead is disclosed. The advantages of the DIDS spinal cord stimulator lead that may be obtained in various embodiments can include resolving the issues associated with lead migration. Through percutaneous means, and using the technique as referenced above, embodiments can be implemented in which the practitioner may be afforded control of the entire length of the spinal cord stimulator lead. This is an advancement over the time tested Seldinger Technique catheter over wire procedure. Traditional stimulators only allow for one end of control allowing the distal end to be mobile. By securing both ends, the DIDS spinal cord stimulator lead corrects this issue simply without the need of added complexity and danger to the patient.

Additionally, having two ports of access allows for two IPG (implantable pulse generator) units attached to either ends (proximal or distal) of the spinal cord stimulator lead. The IPG units at either the proximal or distal ends in the DIDS spinal cord stimulator lead are outside the spinal canal and epidural space. The DIDS IPG units have many advantages as compared to traditional one IPG unit stimulators and leads. The battery for the IPG units can be smaller thus allowing for placement and retrieval by percutaneous means rather than a pocket surgery typically needed for traditional stimulators that require larger battery types. The distal and proximal ends can be configured with removable and replaceable IPG units. This will allow practitioners, at a later date, the ability to change or replace the IPG units with units that provide higher, lower or stronger pulses or frequencies. This also allows for easy removal of the internal hardware and software if an update, change or replacement is needed. The middle portion of the spinal cord stimulator DIDS spinal cord stimulator lead provides the circuitry and stimulation electrode points where electrical charge can be provided to the target areas along the Dura for pain relief.

In another iteration of the DIDS spinal cord stimulator lead, the EDIDS (Expandable dual input, dual source) spinal cord stimulator lead has a middle portion that is expandable which allows for easier displacement as well as larger surface area coverage for electrode stimulation points. Additionally, the MDIDS (Multi channel dual input dual source) spinal cord stimulator lead provides the added benefit possessing one or two drug pumps. The MDIDS will be able to provide disbursement of medications in the form of liquids, gases, solids and powders that will be easily be placed in the epidural space and potentially the dura itself through a porous lumen which will be connected to either a drug pump or IPG unit on either side of the spinal cord stimulator lead. The MDIDS may also have drug pump capabilities as well as spinal cord simulator capabilities in the same lead that may allow for pain relief that can be accomplished through chemical as well as gait theory distraction stimulation. These capabilities provide practitioner with a more advanced tool to be able to offer greater relief to the patient. The distal and proximal end of the MDIDS spinal cord stimulator lead may have either a pain pump and or an IPG unit at either end. The two ports allow for a proximal and or distal drug pump that solves a number of issues through redundancy. If one port becomes clogged the other port will be continue to function. This redundancy allows for continuous medication and can help prevent a disastrous event if one port becomes clogged.

The Dual Port Catheter Drug Pump Delivery System may be placed and secured within the epidural space along any desired target area of the dura of the spinal cord within the patient's spine canal. The Dual Port Catheter Drug Pump Delivery System DPCDPD allows for drug delivery using two ports of access that is independent of the MDIDS lead, which possess combined drug pump and spinal cord stimulator capabilities.

Additionally, the disclosure herein describes a Self Contained Spinal Cord Stimulator SCSCS where the SCSCS is a lead which may be used to house the software, hardware, computing capabilities, IPG unit, Battery source, stimulator electrodes, circuitry (including flexible circuit boards), connecting wires needed to propagate a charge. The SCSCS proximal end and a distal end may be used to anchor via suture, button, wire mechanism or other fixation mechanism readily known in the art for stability within the epidural space or outside the epidural space, however the practitioner sees fit. The SCSCS possess within its elongate body the ability to compute, transfer data and generate a stimulation pulse without need of an IPG unit outside the epidural space as compared to traditional spinal cord stimulator leads.

The SCSCS lead contains all structures necessary to provide propagation of current and stimulation of the targeted dura. Additionally, the SCSCS is capable to receive and send information in and out of the patient's body without hard wire interface. The computer capability and firmware/software aspects may be completely housed within the SCSCS within the epidural space. The spinal cord stimulator may have wireless capabilities. Wireless communication may be any one of the applicable standards or a custom protocol including WiFi (802.11a/b/g/n), Bluetooth®, Zigbee®, or a custom protocol over the dedicated medical body-area network within the FCC assigned spectrum. In so doing, the patient or practitioner will be able to program or control the SCSCS from outsides the patient's body. Power to the stimulate unit may be provided by way of a battery that may be inside the epidural space, completely enclosed within the lead itself or partially exposed for ease of exchange. Computer processing may be based on an FPGA, ASIC, hybrid analog-digital ASIC, or general-purpose processor. The SCSCS IPG unit may also traverse the entire length of the spinal cord stimulator and may be comprised of flexible circuits or miniaturized. The SCSCS may be able to charge its battery through wireless technology where a transmitter will be on the outside of the patient's body and able to recharge the battery within the patient's body without direct contact, e.g., by induction.

The plurality of spinal stimulators leads discussed possess the ability to share information, current and functionality within the epidural space through connection ports side-by-side with other stimulators. This allows for shared current and shared information where the devices can work in conjunction with each other spinal cord stimulators to allow for greater surface area and greater pain relief. The plurality of discussed spinal cord stimulator leads possess malleable qualities that allow for flexion and extension that is compatible with the movement within the epidural space. Additionally, the embodiments of the technology disclosed herein possess the ability to vibrate at desired frequencies.

Another aspect of a spinal cord stimulator lead is disclosed. A spinal cord stimulator lead includes a proximal portion that is configured for placement within the human anatomy at a first location, a distal portion that is configured for placement within the human anatomy at a second location, and a middle portion that is configured for percutaneous placement in an epidural space, wherein said middle portion includes at least one stimulator electrode for placement adjacent to target dura.

An aspect of an electrical stimulator lead is also disclosed. An electrical stimulator lead includes a self-contained elongate that is configured to be percutaneously inserted into the human anatomy, wherein said self-contained elongate further comprises, a proximal portion that is configured for placement within the human anatomy at a first location, a distal portion that is configured for placement within the human anatomy at a second location, and a middle portion that is configured for percutaneous placement near a target treatment area, wherein said middle portion includes at least one stimulator electrode.

Various embodiments may be implemented in which the practitioner has access to both distal and proximal ends as described, this allows anchoring of the proximal and/or distal segments of the stimulator, thus eliminating or minimizing issues with lead migration. Additionally, other embodiments disclosed herein include drug pump capabilities and a stimulator lead that may contain all the necessary components to provide user interaction and propagation of pulse energy for pain relief with contact outside the epidural space and the spinal canal. The embodiments described may be placed at any level of the spinal cord.

It is understood that other aspects of the technology disclosed herein may become readily apparent to those of ordinary skill in the art from the following detailed description, wherein it is shown and described only various aspects of the invention by way of illustration. As will be realized, the invention is capable of other and different configurations and its several details are capable of modification in various other respects, all without departing from the scope of the invention. Accordingly, the drawings and detailed description are to be regarded as illustrative in nature and not as restrictive.

BRIEF DESCRIPTION OF DRAWINGS

Various aspects of the illustrative embodiments will be described herein using terms commonly employed by those skilled in the art to convey the substance of their work to others skilled in the art. However, it will be apparent to those skilled in the art that the embodiments of the technology disclosed herein may be practiced with only some of the described aspects. For purposes of explanation, specific numbers, materials and configurations are set forth in order to provide a thorough understanding of the illustrative embodiments. However, it will be apparent to one skilled in the art that the disclosed technology may be practiced without the specific details. In other instances, well-known features are omitted or simplified in order not to obscure the illustrative embodiments.

FIGS. 1-5 (prior art) illustrate various conventional spinal cord stimulator leads implanted in an epidural space.

FIG. 6 is a top view of a dual input, dual source spinal cord lead (DIDS).

FIG. 7 is a view of the expandable dual input, dual source spinal cord lead (EDIDS).

DETAILED DESCRIPTION

Figure 4:
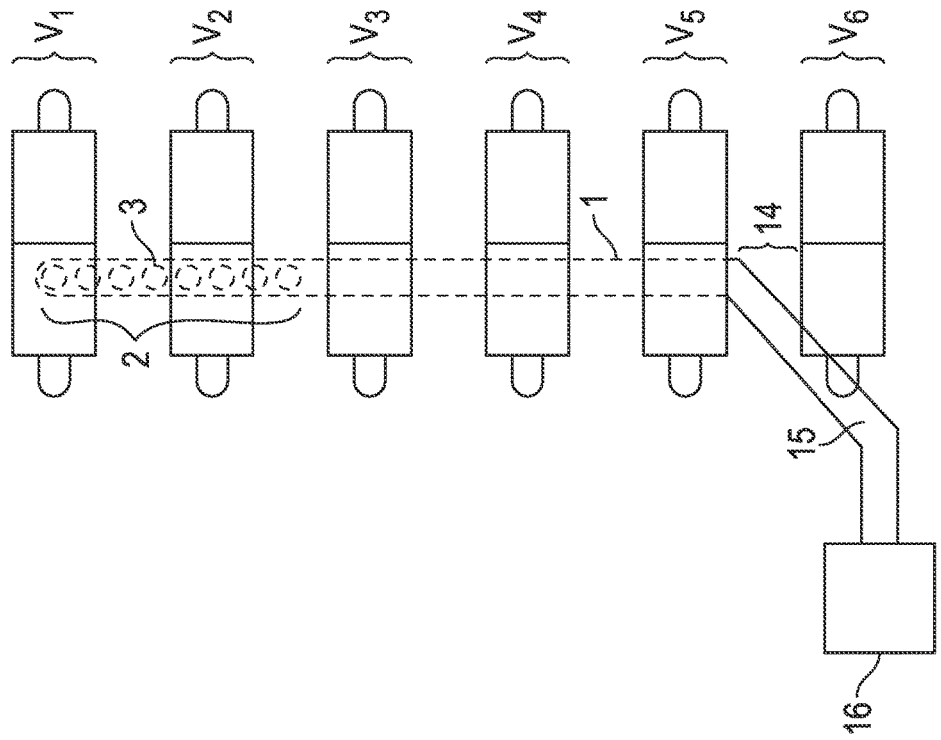

FIGS. 1 and 2 (prior art) illustrate conventional spinal cord stimulator leads. FIG. 1 is a top view of a conventional spinal cord stimulator lead. The distal end 2 of the conventional spinal cord stimulator may be placed in the epidural space (not shown). The distal end 2 of the conventional spinal cord stimulator lead may contain electrodes in the form of a paddle, represented in FIG. 2 as the distal stimulator electrodes or DSE 3. The distal stimulator electrodes (DSE) 3 may vary in number typically 4, 8, 16, 32 or more. In FIG. 1, the distal stimulator electrodes (DSE) 3 are depicted as eight DSE at the distal end 2. The distal end 2 containing the DSE 3 may be placed above the desired target area of the dura (not shown) of the spinal cord where the DSE 3 may stimulate the dura of the spinal cord (not shown). In a conventional spinal cord stimulator lead, the distal end 2 and the distal stimulator electrodes DSE 3 enter the epidural space (not shown) from a point lower in the spinal cord (not shown) and never exits the epidural space. The middle portion 1 of the conventional spinal cord stimulator lead connects the distal end 2 (that remains inside the patient) and the proximal end 15 (that enters and exits the patient). The practitioner placing the conventional spinal cord stimulator lead inside the patient in the epidural space of the spine only has control of the proximal end 15 of the conventional spinal cord stimulator. The practitioner placing the conventional spinal cord stimulator lead may only control the distal end 2 of the traditional spinal cord stimulator by manipulating the proximal end 15. The proximal end 15 of a conventional spinal cord stimulator lead may be attached to an IPG (pulse generating device) unit and/or battery unit (outside the epidural space). The distal end 2 enters the epidural space at the same point where the proximal end 15 exits from.

FIG. 2 is one view of a surgical spinal cord stimulator lead, the distal end 2 of the surgical spinal cord stimulator lead may be placed in the epidural space (not shown) typically by surgical open technique that may require partial laminotomy. The distal end 2 of the surgical spinal cord stimulator lead contains electrodes in the form of a paddle, represented in FIG. 2 as the distal stimulator electrodes (DSE) 3, the DSE may vary in number typically 4, 8, 16, 32 or more. In FIG. 2, the distal stimulator electrodes 3 number sixteen. The distal end 2 containing the distal stimulator electrodes 3 may lie above the desired target area of the dura of the spinal cord where the distal stimulator electrodes DSE 3 may stimulate the dura of the spinal cord (not shown). In a surgical spinal cord stimulator lead, the distal end 2 and the distal stimulator electrodes DSE 3 enter the epidural space (not shown) from a point lower in the spinal cord and never exits the epidural space. The middle portion 1 of the surgical spinal cord stimulator lead connects the distal end 2 (that remains inside the patient) and the proximal end 15 (that enters and exits the patient). The practitioner placing the surgical spinal cord stimulator lead inside the patient in the epidural space of the spine only has control of the proximal end 15 of the surgical spinal cord stimulator. The practitioner placing the surgical spinal cord stimulator lead may only control the distal end 2 of the surgical spinal cord stimulator lead by manipulating the proximal end 15. The proximal end 15 of a surgical spinal cord stimulator lead may be attached to an IPG (pulse generating device not shown) unit or battery unit (not shown) outside the epidural space. The distal end 2 enters the epidural space (not shown) at the same point where the proximal end 15 exits.

Figure 3:
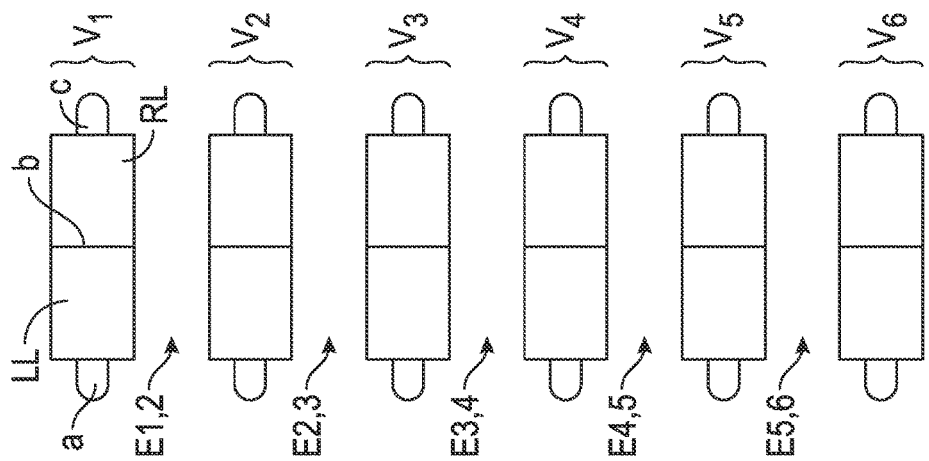

FIG. 3 is a front view of a normal human spine. In the front and side views of a the human spine there are 7 cervical vertebrae (C1, C2, C3, C4, C5, C6, C7), 12 thoracic vertebra (T1, T2, T3, T4, T5, T6, T7, T8, T9, T10, T11, T12), lumbar vertebrae (L1, L2, L3, L4, L5) and Sacral and Coccyx bones. FIG. 3 is a schematic representation of six vertebrae in continuity with each other. The six vertebrae, vertebra 1 (V1), vertebra 2 (V2), vertebra 3 (V3), vertebra 4 (V4), vertebra 5 (V5) and vertebra 6 (V6) may represent any six continuous vertebrae of the spine. In one example of how FIG. 3 may schematically demonstrate a portion of the posterior aspect of the spine, V1 may represent C1 (cervical vertebra 1) and V2 may represent C2 (cervical vertebra 2), V3 may represent C3, V4 may represent C4, V5 may represent C5 and V6 may represent C6. In another example of how FIG. 3 may schematically demonstrate a portion of the spine, V1 may represent T12 (thoracic vertebra 12) and V2 may represent L1 (lumbar vertebra 1), V3 may represent L2 (lumbar vertebra 2), V4 may represent L3 (lumbar vertebra 3), V5 may represent L4 (lumbar vertebra 4) and V6 may represent L5 (lumbar vertebra 5).

FIG. 3 illustrates the posterior aspect of a spine depicting six vertebra along the spine. The posterior aspect of each vertebra respectfully consists of a left transverse process (a), left lamina (LL), spinous process (b), right lamina (RL) and right transverse process (c). The potential space of the epidural space may be described by its adjacent vertebral anatomy where the epidural space between V1 and V2 may be labeled E1, 2. The epidural space between V2 and V3 may be labeled E2, 3. The epidural space between V3 and V4 may be labeled E3, 4. The epidural space between V4 and V5 may be E4, 5. The epidural space between the V5 and V6 may be E5, 6.

FIG. 4 demonstrates a conventional spinal cord stimulator in the epidural space placed by percutaneous means. The distal end 2 and the distal stimulator electrodes DSE 3 are within the epidural space lying superior to the spinal cord and directly below V1 and V2. The conventional spinal cord stimulator may be seen as entering the epidural space at an entrance point 14 and seen traversing up the spine. The conventional spinal cord stimulator may be seen having a proximal portion 15 that enters the epidural space at entrance point 14 between V5 and V6. The middle portion 1 of the conventional spinal cord stimulator connects the distal end 2 that remains inside the patient and the proximal end 15 that enters and exits the patient at entrance point 14. The proximal portion 15 may be the only part of the conventional spinal cord stimulator that remains outside the patient's body. The conventional spinal cord stimulator distal portion 2, distal stimulating electrodes DSE 3, the middle portion 1 all remain inside the patient's body within the epidural space. The proximal portion 15 may be seen here connecting to an IPG (implantable pulse generator) unit 16 outside of the patient's spine.

Figure 5:
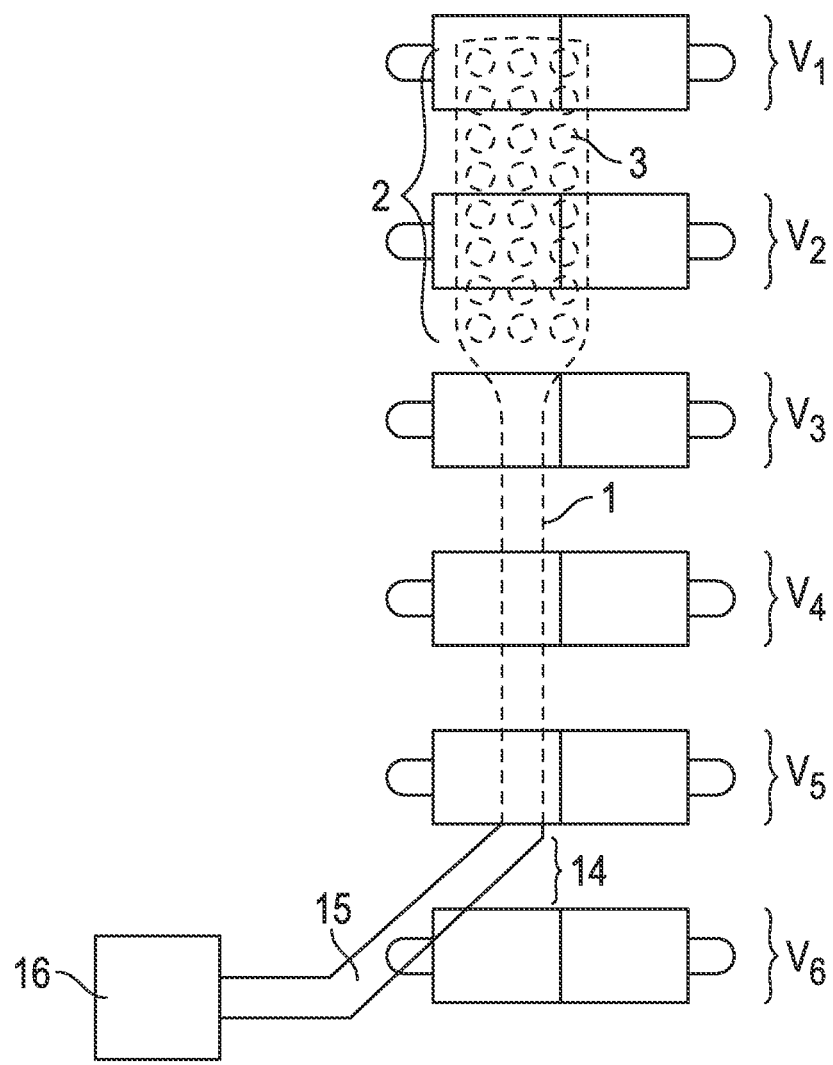

FIG. 5 demonstrates a surgical spinal cord stimulator in the epidural space placed by surgical open technique that may require partial laminotomy. The distal end 2 and the distal stimulator electrodes DSE 3 are within the epidural space lying superior to the spinal cord and directly below V1 and V2. The surgical spinal cord stimulator may be seen as entering the epidural space at an entrance point 14 and seen traversing up the spine. The surgical spinal cord stimulator may be seen having a proximal portion 15 that enters the epidural space at entrance point 14 between V5 and V6. The middle portion 1 of the surgical spinal cord stimulator connects the distal end 2 that remains inside the patient and the proximal end 15 that enters and exits the patient at entrance point 14. The proximal portion 15 may be the only part of the surgical spinal cord stimulator that remains outside the patient's body. The surgical spinal cord stimulator distal portion 2, distal stimulating electrodes DSE 3, the middle portion 1 all remain inside the patient's body within the epidural space. The proximal portion 15 may be seen here connecting to an IPG (implantable pulse generator) unit 16 outside of the patient's spine.

The various embodiments disclosed herein may be implemented using the techniques disclosed in PERCUTANEOUS METHODS FOR SPINAL STENOSIS AND FORAMINAL STENOSIS for which a United States utility patent application was filed on Jul. 17, 2012, under Ser. No. 13/551,166, and a PCT application was filed on Jul. 17, 2012, under Ser. No. PCT/US12/47050. The surgical techniques and apparatuses described therein may also be referred to herein as the "T-Technique."

In a first exemplary embodiment, FIG. 6 is a top view of a dual input, dual source spinal cord lead (DIDS) 60. The dual input dual source spinal cord stimulator lead 60 has a proximal part 69 that may connect to a proximal IPG unit 66b and distal part 64 that connects to a distal IPG unit 66a. The dual input, dual source spinal cord lead 60 has both its distal part 64 and proximal part 69 outside the patient's body (not shown). The middle stimulator paddle portion 66 contains the middle stimulator electrodes MSE 68, which may vary in number but typically 4, 8, 16, 32 or more. As depicted in FIG. 6, the middle stimulator electrodes MSE 68 number eight and are represented by eight circle like figures. The middle portion 62 is composed of the distal middle portion 65, the proximal middle portion 67 and the middle stimulator paddle portion 66 with middle stimulator electrodes MSE 68. The middle portion 62 of the dual input, dual source spinal cord stimulator lead 60 resides completely within the patient's body (not shown). The middle portion 62 of the dual input dual source spinal cord stimulator lead DIDS 60 may be entered into the epidural space (not shown) of the spinal cord (not shown) by percutaneous epidural needles using the percutaneous technique previously discussed. The middle portion 62 of the dual input dual source spinal cord stimulator DIDS 60 may be controlled outside the patient's body by a practitioner by manipulating the distal end 64 and/or the proximal end 69. The practitioner having control of both the distal end 64 and proximal end 69 with middle portion 62 within the body thus has the ability to control the middle portion 62 by pulling the distal end 64 or proximal end 69 in a backward or forward motion, as needed. As the practitioner may be able to control the distal portion 64 and proximal portion 69 of the dual input dual source spinal cord stimulator lead 60, the practitioner also has control of the middle portion 62 where the middle stimulator paddle portion 66 and the middle stimulator electrodes MSE 68 may then be maneuvered by pulling or pushing motion described above to the desired target area of the dura of the spinal cord (not shown) where the middle stimulator paddle portion 66 and the middle stimulator electrodes MSE 68 may stimulate the targeted area overlaying the dura of the spinal cord (not shown).

The dual port dual source spinal cord stimulator lead DIDS 60 has a distal end 64 and proximal end 69 that may be outside the patient's body (not shown). The distal end 64 and the proximal end 69 may have many functions including the above described control of the middle portion 62 of the dual input dual source spinal cord stimulator lead DIDS 60. Furthermore, the distal end 64 may connect to an IPG unit 66a and the proximal end 69 may connect to an IPG unit 66b. Additionally, the distal end 64 and proximal end 69 may be connected to each other to form a ring (not shown) outside the patient. Also, the distal end 64 and the proximal end 69 may be secured in a way outside the epidural space (not shown) that will prevent the middle portion 62 of the dual port dual source spinal cord stimulator lead DIDS 60 from migrating from targeted area of dura of the spinal cord in the epidural space of the spine (not shown). By securing the distal portion 64 and the proximal portion 69 using well-known anchoring methods outside the epidural space and with the middle portion 62 now fixed in a desired location in the epidural space, with the middle stimulator paddle portion 66 and the middle stimulator electrodes MSE 68 immobile and locked in a targeted area of dura of the spinal cord, the practitioner may effectively prevent the issue of migration of paddles and thus eliminate the issue of lead migration seen in conventional spinal cord stimulator leads or surgical stimulator leads (FIGS. 1-5).

By way of non-limiting examples, the benefit of having two IPG units (distal IPG 66a and proximal IPG 66b) gives the patient and practitioner added advantage of extended battery life, and smaller IPG units as compared to traditional one port stimulators (conventional percutaneous and surgical spinal cord stimulator leads). The IPG units 66b, 66a may have different frequency output where one IPG unit may be of high frequency and the other IPG unit may be of low frequency. The IPG units may have different polarity where one IPG unit 66b may be negative and the other IPG unit 66a may be positive.

FIG. 7 is a view of the expandable dual input, dual source spinal cord lead EDIDS 70. The expandable dual input dual source spinal cord stimulator lead EDIDS 70 has a proximal part 79 that connects to a proximal IPG unit 72 and distal part 74 that connects to a distal IPG 72a. The expandable dual input dual source spinal cord lead EDIDS has both its distal part 74 and proximal part 79 outside the patient's body (not shown). The middle stimulator paddle portion 76 that contains the middle stimulator electrodes MSE 78, may vary in number typically 4, 8, 16, 32 or more. In FIG. 7, the middle stimulator electrodes MSE 78 number twenty-two. The middle stimulator paddle portion 76 of the expandable dual input, dual source spinal cord stimulator lead EDIDS 70 has many functions and expandable capabilities. The middle stimulator paddle portion 76 initially may be folded or rolled up upon itself and once inside the epidural space may expand by electronic, magnetic, pressure, memory form metals and alloys, nanotechnology, graphene components, hydraulics and/or mechanical means. The middle stimulator paddle portion 76 has ability to contract back to initial size and fold up or roll upon itself if the practitioner wishes to remove the expandable dual input dual source spinal cord lead EDIDS 70 at a later date.

The middle portion 71 may be composed of the distal middle portion 75, the proximal middle portion 77 and the middle stimulator paddle portion 76 with middle stimulator electrodes MSE 78. The middle portion 71 of the expandable dual input, dual source spinal cord stimulator EDIDS lead 70 may reside completely within the patient's body (not shown). Additionally, the middle stimulator paddle portion 76 may have a negative pressure or positive pressure balloon for placement and securing properties. The middle stimulator paddle 76 may have the ability to be mobile where the practitioner by methods and means outside the patient's body may control the placement of the middle stimulator paddle by rotation, magnets, hydraulics, electronics, mechanical means, and/or pulley system where the middle stimulator paddle portion 76 may traverse up and down the middle portion 71 of the expandable dual input dual source spinal cord stimulator lead EDIDS 70 within the epidural space of the spine (not shown). The middle portion 71 of the expandable dual input dual source spinal cord stimulator lead EDIDS 70 may be entered into the epidural space (not shown) of the spinal cord (not shown) by percutaneous epidural needles (not shown) using the percutaneous technique described above. The middle portion 71 of the expandable dual input dual source spinal cord stimulator EDIDS 70 may be controlled outside the patient's body by a practitioner by manipulating the distal end 74 and/or the proximal end 79. The practitioner having control of both the distal end 74 and proximal end 79 with middle portion 71 within body thus has the ability to control the middle portion 71 by pulling the distal end 74 or proximal end 79 in a backward or forward motion. As the practitioner may be able to control the distal portion 74 and proximal portion 79 of the expandable dual input dual source spinal cord stimulator lead EDIDS 70, the practitioner also has control of the middle portion 71 where the middle stimulator paddle portion 76 and the middle stimulator electrodes MSE 78 may then be maneuvered by pulling motion described above to the desired target area of the dura of the spinal cord (not shown) where the middle stimulator paddle portion 76 and the middle stimulator electrodes MSE 78 may stimulate the targeted area overlaying the dura of the spinal cord (not shown).

The expandable dual port dual source spinal cord stimulator lead EDIDS 70 has a distal end 74 and proximal end 79 that may be outside the patient's body (not shown). The distal end 74 and the proximal end 79 have many functions including the above described control of the middle portion 71 of the expandable dual input dual source spinal cord stimulator lead EDIDS 70. Furthermore, the distal end 74 may connect to an IPG unit 72a and the proximal end 79 may connect to an IPG unit 72. Additionally, the distal end 74 and proximal end 79 may be connected to each other to form a ring (not shown) outside the patient. Additionally, the distal end 74 and the proximal end 79 may be secured in a way outside the epidural space (not shown) that will prevent the middle portion 71 of the expandable dual port dual source spinal cord stimulator lead EDIDS 70 from migrating from targeted area of dura of the spinal cord in the epidural space of the spine (not shown). By securing the distal portion 74 and the proximal portion 79 by anchoring methods outside the epidural space (not shown) and with the middle portion 71 now fixed in a desired location in the epidural space, (not shown) with the middle stimulator paddle portion 76 and the middle stimulator electrodes MSE 78 immobile and locked in a targeted area overlaying the dura of the spinal cord, the practitioner may thus effectively prevent the issue of migration of paddles and thus eliminate the issue of lead migration seen in conventional spinal cord stimulator leads or surgical stimulator leads.

By way of non-limiting example, the benefit of having two IPG units (distal IPG 72a and proximal IPG 72) gives the patient and practitioner added advantage of extended battery life, smaller IPG units as compared to traditional one port stimulators (conventional percutaneous and surgical spinal cord stimulator leads). The IPG units 72, 72a may have different frequency output where one IPG unit may be of high frequency and the other IPG unit may be of low frequency. The IPG units 72, 72a may have different polarity where the one IPG unit may be negative and the other IPG unit may be positive.

Figure 8:
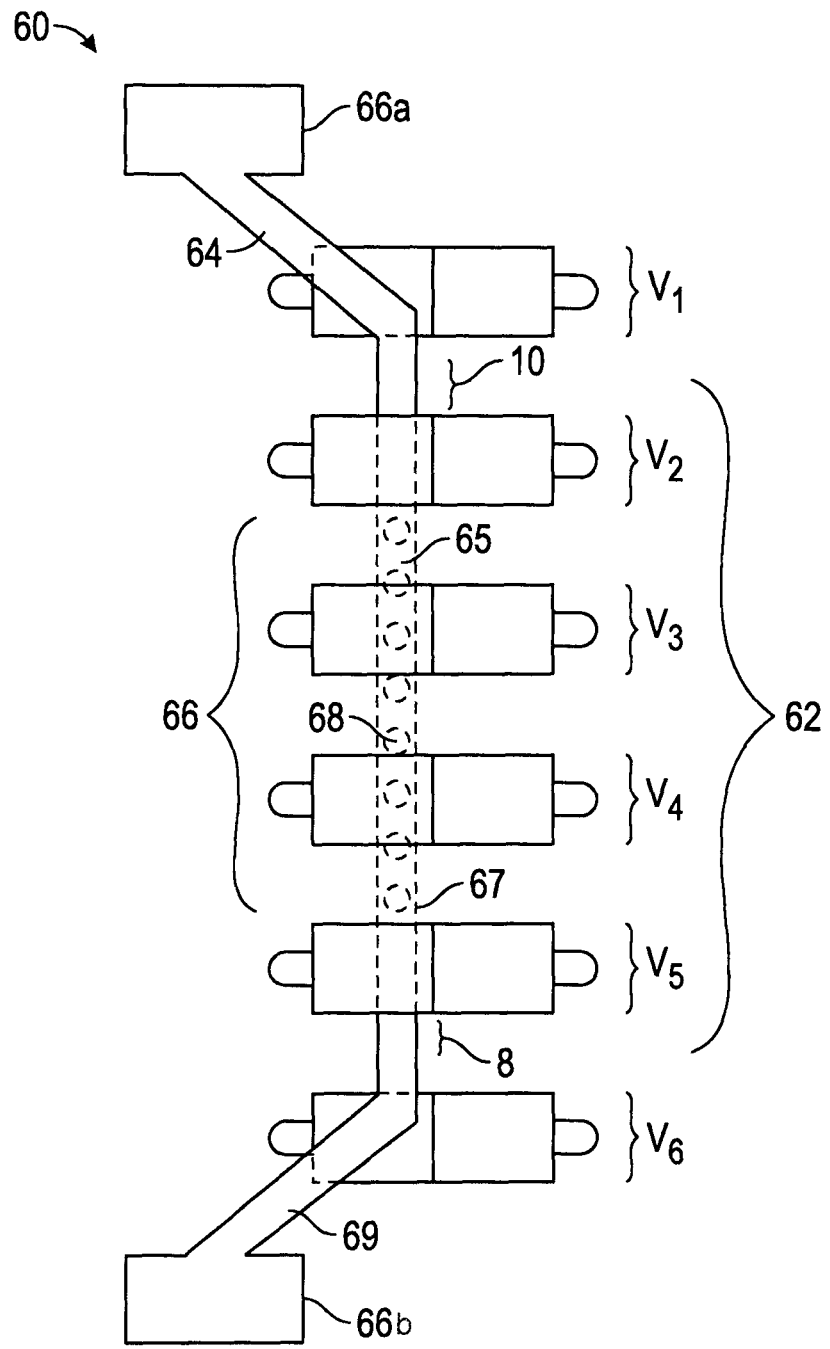
FIG. 8 is a perspective view demonstrating on a spine model the dual input dual source spinal cord stimulator lead DIDS in the epidural space.

FIG. 8 is a perspective view demonstrating on a spine model the dual input dual source spinal cord stimulator lead DIDS 60 in the epidural space that has two positions that exit the spinal canal, a proximal end 69 and a distal end 64 leaving a middle portion 62 firmly secured in the epidural space of the spine (not shown).

The dual input dual source spinal cord stimulator lead DIDS 60 may be any length in size. The dual input dual source spinal cord stimulator lead DIDS 60 may be utilized in the cervical region of the spine, thoracic region of the spine, lumbar region of the spine and sacral region of the spine. The dual input dual source spinal cord stimulator lead DIDS 60 may be placed anywhere along the spine traversing one or many levels of the spine. In this schematic representation only 6 vertebrae (V1 through V6) are demonstrated for understanding. The actual length of the dual source dual action spinal cord stimulator lead DIDS 60 may extend at a minimum of one vertebra level or may extend from L5/S 1 (prior art C) to C1 /C2 (prior art C).

As the T-Technique has potential to be applied to any part of the spine, the dual input dual source spinal cord stimulator DIDS 60 using methods described by the T-Technique may be placed and secured within the epidural space along any desired target area of the dura of spinal card within the patient's spine.

The dual input dual source spinal cord stimulator lead 60 has a proximal part 69 that connects to a proximal IPG unit 66*b* and distal part 64 that connects to a distal proximal IPG 66*a*. The dual input, dual source spinal cord lead DIDS 60 has both its distal part 64 and proximal part 69 outside the patient's body. The middle stimulator paddle portion 66 that contains the middle stimulator electrodes 65 which may vary in number typically 4, 8, 16, 32 or more. In FIG. 8, the middle stimulator electrodes 65 number eight and are represented by eight circle like figures. The distal end 64 of the dual input dual source spinal cord stimulator lead DIDS 60 exits the spinal cord between V1 and V2 through at the exit point 10. The proximal end 69 of the dual input dual source spinal cord stimulator DIDS 60 enters the spinal cord between V5 and V6 through the entrance point 8. The middle portion 62 of the dual input dual source spinal cord stimulator lead DIDS 60 may be entered into the epidural space of the spinal cord (not shown) by percutaneous epidural needles (not shown) using T-Technique. The middle portion 62 of the dual input dual source spinal cord stimulator DIDS 60 may be controlled outside the patient's body by practitioner by manipulating the distal end 64 and or the proximal end 69. The practitioner having control of both the distal end 64 and proximal end 69 with middle portion 62 within body thus has the ability to control the middle portion 62 by pulling the distal end 64 or proximal end 69 in a backward or forward motion.

As the practitioner may be able to control the distal portion 64 and proximal portion 69 of the dual input dual source spinal cord stimulator lead 60, the practitioner also has control of the middle portion 62 where the middle stimulator paddle portion 66 and the middle stimulator electrodes 65 may then be maneuvered by pulling motion described above to the desired target area of the dura of the spinal cord where the middle stimulator paddle portion 66 and the middle stimulator electrodes 65 may stimulate the targeted area overlaying the dura of the spinal cord (In FIG. 8, the dual input dual port spinal cord stimulator DIDS 60 middle portion 62 may be seen laying beneath the V2,V3, V4, and YS where the middle stimulator paddle portion 66 and middle stimulator electrodes 65 may be seen laying beneath V2,V3,V4).

Figure 9:
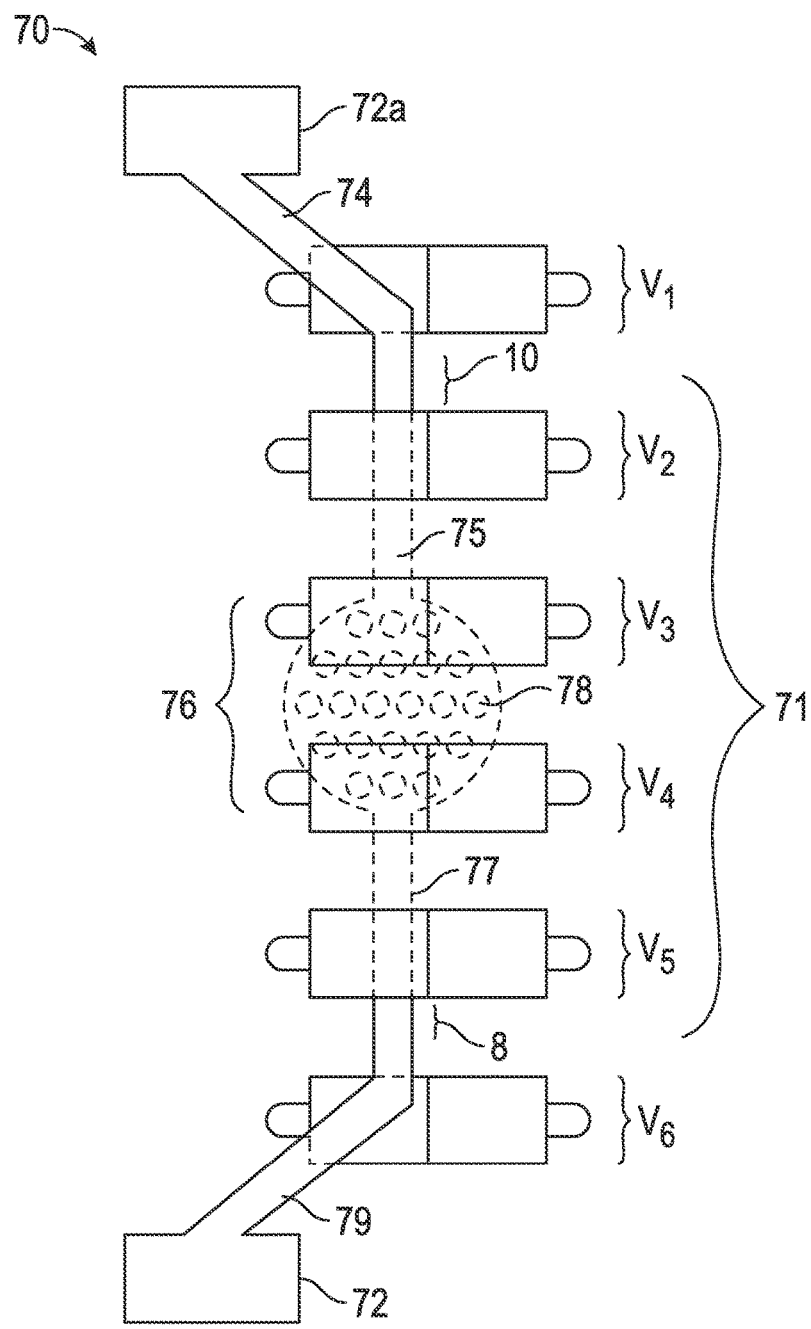
FIG. 9 is a perspective view of the expandable dual input, dual source spinal cord lead (EDIDS) in the epidural space.

FIG. 9 is a schematic view of the expandable dual input, dual source spinal cord lead (EDIDS) 70 in an epidural space. The expandable dual input dual source spinal cord stimulator lead EDIDS 70 with the middle portion 71 secured in the epidural space the proximal end 79 and distal end 74 outside the patient's body. The vertebrae (V1, V, V3, V4, V5 and V6) may represent any six or more consecutive vertebrae of a spine. FIG. 9 is a schematic representation describing the expandable dual input dual source spinal cord stimulator EDIDS 70 in that it has two positions that exit the spinal canal, a proximal end 79 and a distal end 74 leaving a middle portion 71 firmly secured in the epidural space of the spine. As a person of ordinary skill in the art may readily appreciate, the expandable dual input dual source spinal cord stimulator lead EDIDS 70 may be any length in size, dependent upon the treatment area. The expandable dual input dual source spinal cord stimulator lead EDIDS 70 may be utilized in the cervical region of the spine, thoracic region of the spine, lumbar region of the spine, and/or sacral region of the spine. The expandable dual input dual source spinal cord stimulator lead EDIDS 70 may also be placed anywhere along the spine traversing one or more levels of the spine. In this exemplary embodiment, only six vertebrae are demonstrated, however, one of ordinary skill in the art may determine that the actual length of the expandable dual source dual action spinal cord stimulator lead EDIDS 70 may extend at a minimum of one vertebra level or may extend from L5/S1 to C1/C2.

As a percutaneous technique of the spine has potential to be applied to any part of the spine, the expandable dual input dual source spinal cord stimulator EDIDS 70 may be placed and secured within the epidural space along any desired target area of the dura of spinal cord within the patient's spine. The expandable dual input dual source spinal cord stimulator lead EDIDS 70 has a proximal part 79 that may connect to a proximal IPG unit 72 and distal part 74 that connects to a distal IPG 72*a*. The expandable dual input, dual source spinal cord lead EDIDS 70 may have both its distal part 74 and proximal part 79 outside the patient's body. The middle stimulator paddle portion 76 contains the middle stimulator electrodes MSE 78. In FIG. 9, the middle stimulator electrodes MSE 78 number fourteen, however one of ordinary skill can opt to use as little as one single electrode or any combination of a plurality of electrodes without departing from the teaching described herein. As depicted in FIG. 9, the distal end 74 of the dual input dual source spinal cord stimulator lead EDIDS 70 exits the spinal cord between V1 and V2 through at the exit point 10. The proximal end of the dual input dual source spinal cord stimulator DIDS enters the spinal cord between V5 and V6 through the entrance point 8. The middle portion 71 of the dual input dual source spinal cord stimulator lead EDIDS 70 may enter the epidural space of the spinal cord by percutaneous epidural needles. The middle portion 71 of the dual input dual source spinal cord stimulator lead EDIDS may be controlled outside the patient's body by a practitioner by manipulating the distal end 74 and/or the proximal end 79. The practitioner may have control of both the distal end 74 and proximal end 79 with middle portion 71 within body thus has the ability to control the middle portion 71 by pulling the distal end 74 or proximal end 79 in a backward or forward motion, as necessary and determined by a practitioner.

As the practitioner may be able to control the distal portion 74 and proximal portion 79 of the dual input dual source spinal cord stimulator lead, the practitioner also has control of the middle portion 71 where the middle stimulator paddle portion 76 and the middle stimulator electrodes MSE 78 may then be maneuvered by pulling motion described above to the desired target area of the dura of the spinal cord where the middle stimulator paddle portion 76 and the middle stimulator electrodes MSE 78 may stimulate the targeted area overlaying the dura of the spinal cord.

Figure 10:
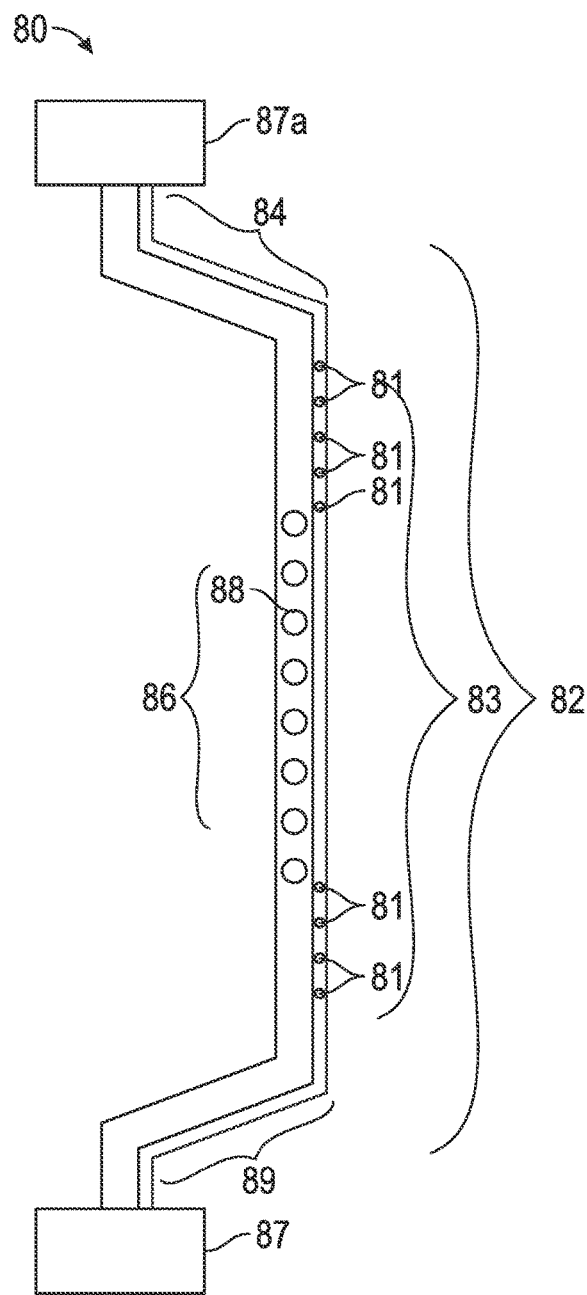
FIG. 10 is a perspective view of the Multi-channel dual input dual source (MDIDS) spinal cord stimulator lead and catheter in the epidural space with a parallel lumen having apertures.

FIG. 10 is a perspective view of a multi-channel dual input, dual source spinal cord lead (MDIDS) 80. The multi-channel dual input dual source spinal cord stimulator lead MDIDS 80 has a proximal end 89 that connects to a proximal unit 87 and distal end 84 that connects to a distal unit 87*a*. The proximal unit 87 and distal unit 87*a* may be an IPG unit or pain pump or both or have the capabilities to be both including capabilities to be interchangeable. The multichannel dual input dual source spinal cord lead MDIDS 80 may have multiple lumens 82 that traverse within it. The lumens 82 may be one, or more in number. In FIG. 10, a schematic view of a lumen 82 may be seen traversing the length of the multichannel dual input dual source spinal cord lead 80 and pain pump MDIDS with a distal part 84, middle part 83 and a proximal part 89.

The multichannel dual input, dual source spinal cord lead MDIDS 80 may have both its distal part 84 and proximal part 89 outside a patient's body. The middle stimulator paddle portion 86 that contains the middle stimulator electrodes MSE 88, may vary in number, typically 4, 8, 16, 32 or more. The middle portion 83 is composed of the distal middle portion, the proximal middle portion, and the middle stimulator paddle portion 86 with middle stimulator electrodes MSE 88. The middle portion 83 of the multichannel dual input, dual source spinal cord stimulator lead MDIDS 80 may reside completely within the patient's body.

The lumen(s) 82 along the middle portion 83 of the multichannel dual input dual source spinal cord lead MDIDS 80 may have multiple pores or apertures 81 where medicines in the form of gas, liquid, solid or other methods of drug delivery known in the art may be released in the epidural space of the spinal cord. The medicines in the form of gas, liquid, solid or other methods of drug delivery known in the art may be stored in wells in either proximal unit 87 or distal unit 87a or both. The middle portion 83 of the dual input dual source spinal cord stimulator lead DIDS 80 may be entered into the epidural space of a spinal cord by percutaneous epidural needles. The middle portion 83 of the dual input dual source spinal cord stimulator DIDS 80 may be controlled outside the patient's body by a practitioner by manipulating the distal end 84 and/or the proximal end 89.

Moreover, the practitioner having control of both the distal end 84 and proximal end 89 with middle portion 83 within the body thus has the ability to control the middle portion 83 by pulling the distal end 84 or proximal end 89 in a backward or forward motion. As the practitioner may be able to control the distal portion 84 and proximal portion 89 of the multichannel dual input dual source spinal cord stimulator lead MDIDS 80, the practitioner also has control of the middle portion 83 where the middle stimulator paddle portion 86 and the middle stimulator electrodes MSE 88 may then be maneuvered by pulling motion described above to the desired target area of the dura of the spinal cord where the middle stimulator paddle portion 86 and the middle stimulator electrodes MSE 88 may stimulate the targeted area overlaying the dura of the spinal cord.

The distal end 84 and the proximal end 89 have many functions including the above described control of the middle portion 83 of the multichannel dual input dual source spinal cord stimulator lead MDIDS 80, furthermore the distal end 84 may connect to an distal unit 87a and the proximal end 89 may connect to a proximal unit 87. Additionally the distal end 84 and proximal end 89 may be connected to each other to form a ring or loop outside the patient. Additionally the distal end 84 and the proximal end 89 may be secured in a way outside the epidural space that will prevent the middle portion 83 of the multichannel dual port dual source spinal cord stimulator lead MDIDS 80 from migrating from targeted area of dura of the spinal cord in the epidural space of the spine. Securing the MDIDS 80 to the patient's body or to itself may be accomplished by using any method readily known in the art, for example, stitching, magnetics, or other coupling forms.

Figure 11:
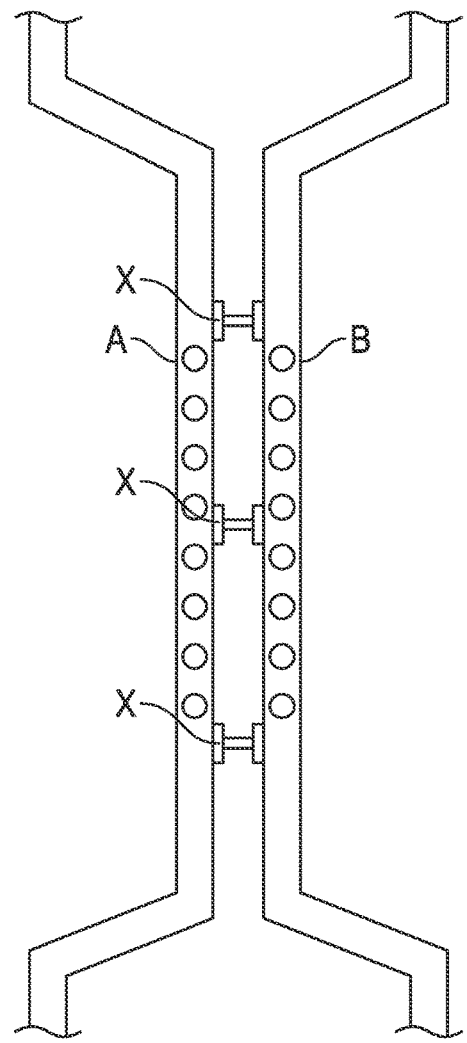
FIG. 11 is a schematic representation of two dual input dual channel spinal cord stimulator leads DIDS connected to each other.

FIG. 11 is a schematic representation of two Dual Input Dual Channel spinal cord stimulator leads DIDS A, B (may also represent expandable and multichannel dual input dual channel spinal cord stimulator leads EDIDS 70, MDIDS 80) demonstrating the ability to connect to one another through interconnection X. Connection X may allow data, energy current, lumens that share medicine to flow between two leads. The connection may also be utilized for stability of the stimulator lead as well.

Figure 12:
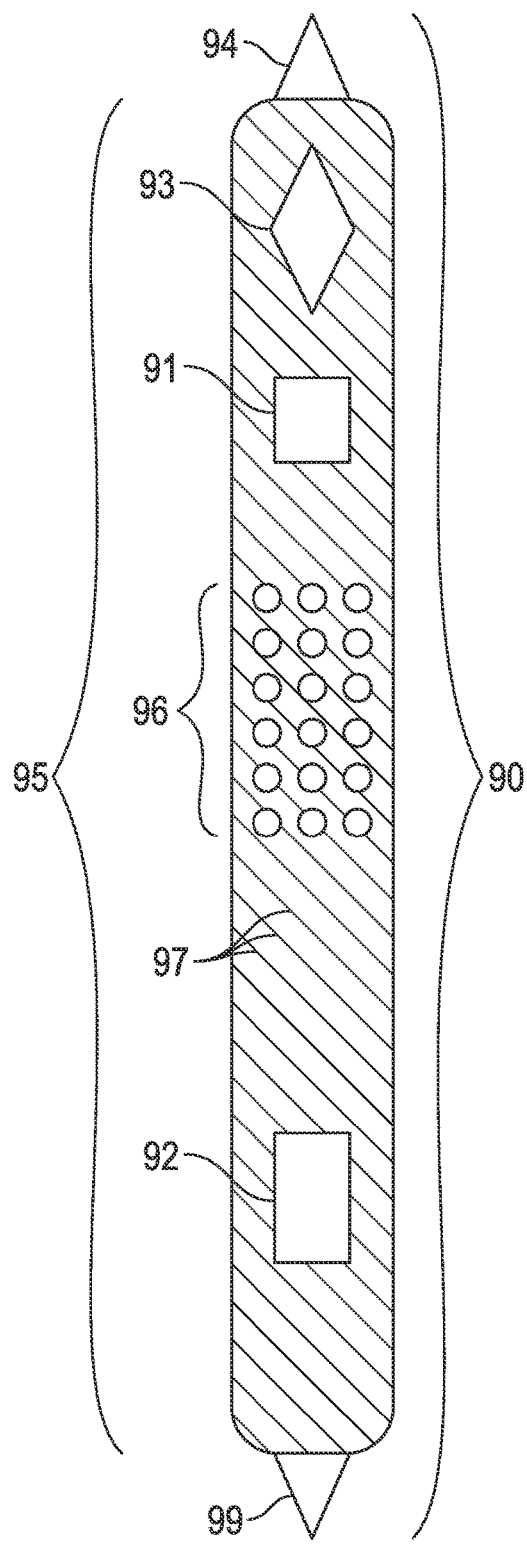
FIG. 12 is a schematic representation of the Self Contained Spinal Cord Stimulator (SCSCS).

FIG.12 is a schematic representation of a Self Contained Spinal Cord Stimulator SCSCS 90 where the lead may be used to house the software, hardware, computer 91, IPG unit 92, and battery source 93, stimulator electrodes 96, flexible circuit board FCB 95, connecting wires 97, all within the stimulator lead itself SCSCS 90 and all within the epidural space (not shown). Through utilizing the percutaneous technique referenced above a proximal end 99 and a distal end 94 may be used to anchor to suture, button, wire mechanisms for stability or by using any other form of fixation mechanism known in the art.

In this exemplary embodiment, the stimulator may be used to house the software, hardware, IPG unit, and/or battery source all within the stimulator lead 90 itself and all within the epidural space in a sealable fashion. All components necessary to provide relief may be housed inside the epidural space with no need for external IPG or computer unit as seen in traditional stimulators to date. Moreover, there is no exit out of the lead outside of the epidural space. The proximal, middle and distal portions of the spinal cord stimulator remain completely within the stimulator lead 90 which may reside in the epidural space. (A connecting piece for fixation of the proximal and/or distal ends may minimally exit the epidural space as necessary.)

Additionally, the battery 93 may be completely enclosed within the stimulator lead 90 itself. The distal 94 and proximal ends 99 of the lead of the spinal cord stimulator 90 may be completely secured within the epidural space. The entire surface area of the lead has potential to act as or contain electrodes 96 such that each particular region or area of the stimulator/lead/electrode can be active or inactive. The areas of active stimulation may be externally programed thus allowing the practitioner to determine the optimal combination of active or inactive stimulation to provide maximal pain relief for the patient. To provide utmost safety and as a result of the fixation at both the proximal 99 and distal ends 94 of the spinal cord stimulator 90, the spinal cord stimulator 90 should allow for the flexion and extension of the spinal cord stimulator that will naturally occur in concert with the patient's movements. Similarly, materials may be of nanotechnology origin, graphene, carbon, metal, plastic, and/or rubber based. Additionally, all of the hardware and all of the software may be located completely within the spinal cord stimulator/lead inside the epidural space.

Power to the stimulate unit 90 may be provided by way of a battery 93 that may be inside the epidural space completely enclosed within the lead 90 itself or partially exposed for ease of exchange. Computer processing may be based on an FPGA, ASIC, hybrid analog-digital ASIC, or general purpose processor. The spinal cord stimulator IPG unit 92 may also traverse the entire length of the spinal cord stimulator and may be comprised of flexible or miniaturized circuits 95. The computing capability and firmware/software aspects may be completely housed within the spinal cord stimulator 90 within the epidural space. The spinal cord stimulator 90 may additionally have wireless capabilities. Wireless communication may be any one of the applicable industry standards, or a custom protocol, including WiFi (802.11 a/b/g/n), Bluetooth®, Zigbee®, or a custom protocol over the dedicated medical body-area network within the FCC assigned spectrum.

The SCSCS 90 may be able to charge its battery 93 that is within the spinal cord stimulator 90 itself within the epidural space through wireless technology where a transmitter will be on the outside of the patient's body and able to recharge the battery 93 within the patient's body without direct contact, e.g., by induction. Wireless interaction may be facilitated by the practitioner or by the device itself via the computer or software. For example, the practitioner may program the computer or software within the spinal cord stimulator through wireless technology. This technology will allow the practitioner the ability to choose which electrodes are active or inactive and in what pattern, either fixed or dynamic over time. Additional electrical parameters may be modified as is readily known to those skilled in the art. For example, wireless technology may also allow the practitioner to determine and programmatically set the strength of the stimulation at each active electrode, the duration of stimulation at each active electrode, the amount of stimulation across all electrodes, location of stimulation, the frequency or frequencies of stimulation and give the practitioner the ability to make changes and program the stimulator to allow for patient to achieve greatest amount of pain relief.

There is also the option to allow for a smartphone application that will provide the patient wireless access to be able to control the spinal cord stimulator for his or herself. This capability will allow the patient to determine the amount of stimulation, what type of stimulation, such as high frequency or low frequency, location such at which electrodes are active or inactive, the length of stimulation, duration of stimulation and other manipulations of the stimulation all through available wireless technology.

The patient and/or practitioner may also capture information and secure upload of that information on the stimulation characteristics through a smartphone or other app to describe patient's feedback on pain level, effective pain stimulation, high vs low frequency to enable practitioner to zero in on the optimal stimulation strategy.

In the latter disclosed embodiment, the lead and the stimulator 90 are one and fit completely inside the epidural space. The battery 93 may be fully contained within the stimulator lead 90. The electrodes 96 may run the length of the stimulator/lead 90. The pattern of stimulation including frequencies, amplitudes, and recruitment of electrodes may be programmable for pain relief. The internal design may be either a single circuit board/single battery or redundant circuit boards/redundant batteries. In the latter case, the circuit boards and batteries may act as backup in a failover architecture or run in parallel with each running its own independent stimulation pattern.

Figure 13:
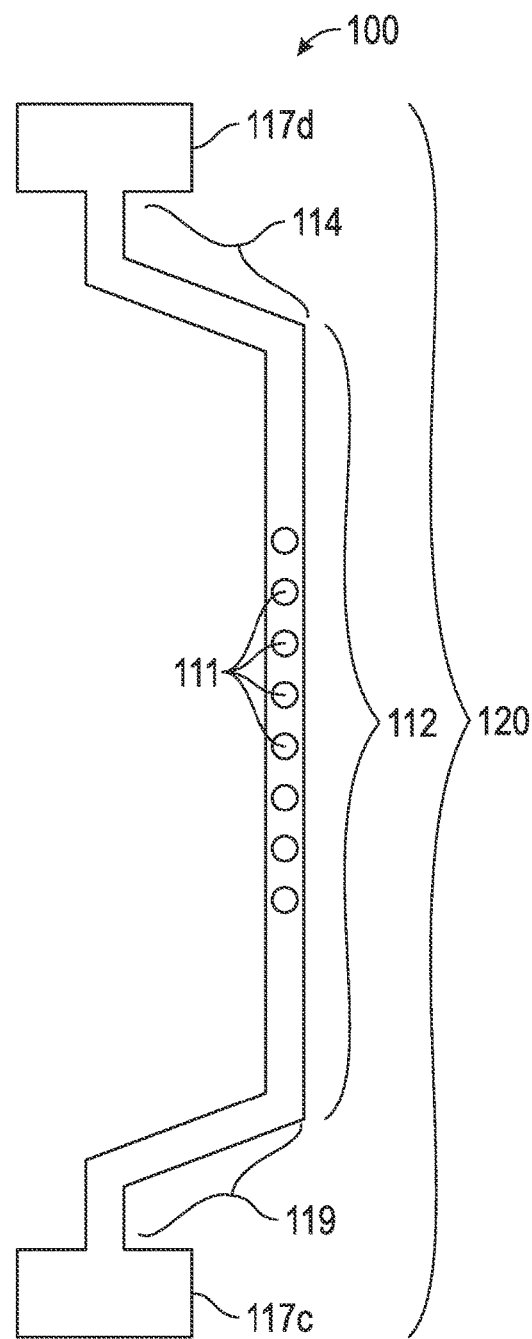
FIG. 13 is a perspective view of the Dual Port Catheter Drug Pump Delivery system (DPCDPD) having a lumen with a plurality of apertures.
Figure 14:
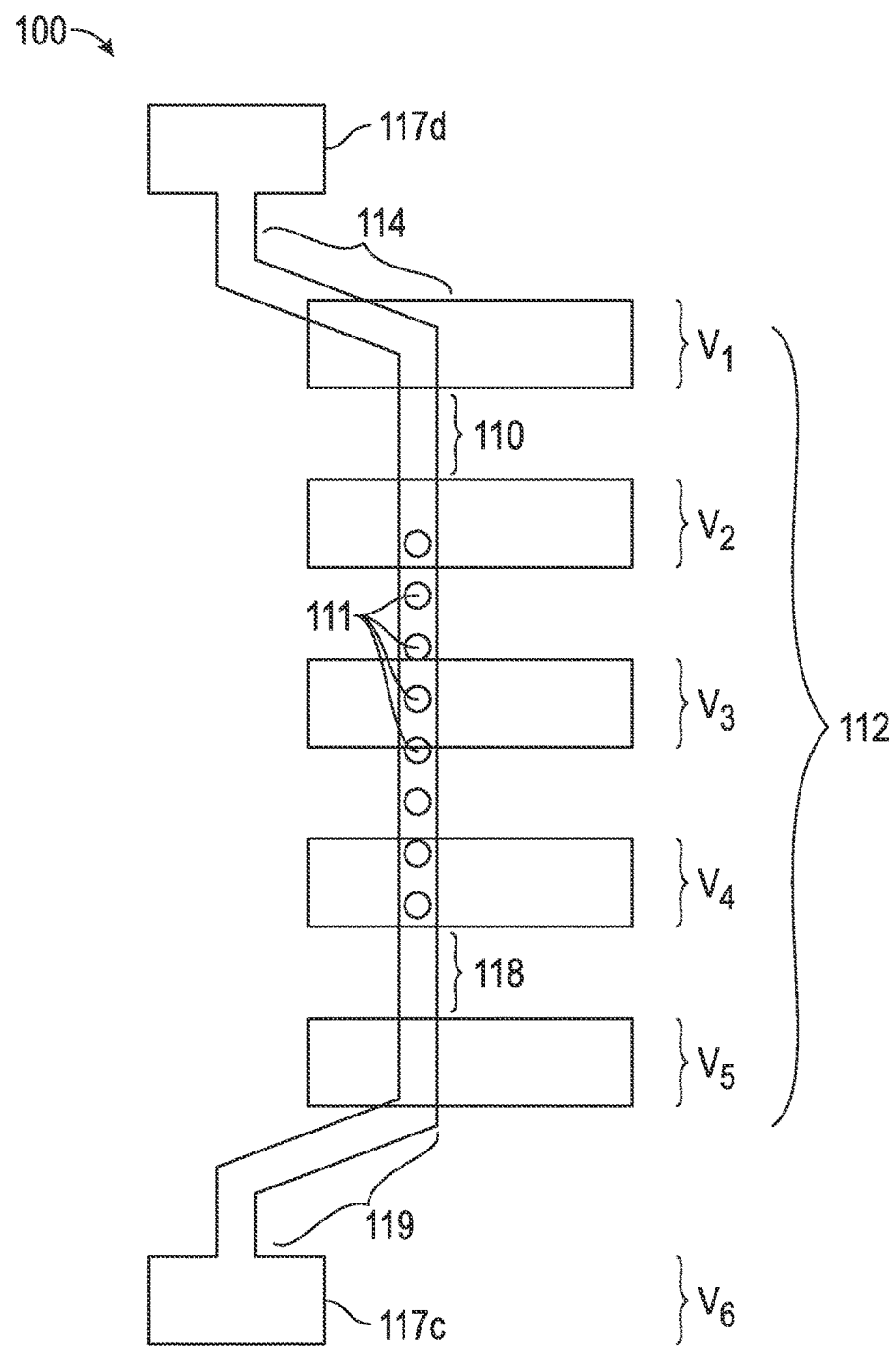
FIG. 14 is a perspective view of the Dual Port Cather Drug Pump Delivery system (DPCDPD) of FIG. 13, wherein the DPCDPD is depicted within the epidural space.

FIGS. 13 and 14 represent the Dual Port Catheter Drug Pump Delivery System that allows for drug delivery using two ports of access that are independent of the MDIDS depicted in FIG. 10, which is a combined dual port pain pump and stimulator representation. FIG. 13 is a view of the Dual Port Catheter Drug Pump Delivery System DPCDPD 100. The Dual Port Catheter Drug Pump Delivery System DPCDPD 100 has a proximal end 119 that connects to a proximal drug pump unit 117c and distal end 114 that connects to a distal drug pump unit 117d. The proximal drug pump unit 117c and distal drug pump unit 117d may be a drug pump delivery system where medicines in the form of gas, liquid, solid or other methods of drug delivery may be stored in wells that may later be pumped into the patient's spine, intrathecal space, and/or epidural space. The Dual Port Catheter Drug Pump Delivery System DPCDPD 100 may have multiple lumens (not shown) that may traverse within its Dual Port catheter 120. The Dual port catheter 120 connects the proximal drug pump unit 117c and the distal drug pump unit 117d with each other. The lumens (not shown) may be one, or more in number.

The dual port catheter 120 of the Dual Port Catheter Drug Pump Delivery System DPCDPD 100 may have both its distal part 114 and proximal part 119 outside the patient's body. The middle portion 112 of the Dual Port Catheter 120 contains one or more lumens (not shown). The lumen(s) (not shown) may have multiple pores or apertures 111 where medicines in the form of gas, liquid, solid or other methods of drug delivery may be released into the epidural space of the spinal cord. In FIG. 13, the Dual Port Catheter 120 displays pores 111 where medicines in the form of gas, liquid, solid or other methods of drug delivery may be stored in wells in either proximal unit 117a or distal unit 117b or both. The Dual Port Catheter 120 of the Dual Port Catheter Drug Pump Delivery System DPCDPD 100 may be entered into the epidural space of the spinal cord by percutaneous epidural needles using the T-Technique. The middle portion 112 of the Dual Port Catheter 120 may be controlled outside the patient's body by a practitioner by manipulating the distal end 114 and/or the proximal end 119. The practitioner having control of both the distal end 114 and proximal end 119 with middle portion 112 within body thus has the ability to control the middle portion 112 by pulling the distal end 114 or proximal end 119 in a backward or forward motion that may then be maneuvered to lay upon the desired target area of the dura or epidural space of the spinal cord. The distal end 114 and proximal end 119 may be used to anchor the dual port catheter 120 once desired positioning of the middle portion 112 is found.

FIG. 14 is a schematic view of a spine model and the Dual Port Catheter Drug Pump Delivery System DPCDPD 100 in the epidural space placed by percutaneous epidural needles using T-Technique. The Dual port catheter 120 connects the proximal drug pump unit 117c and the distal drug pump unit 117d. The Dual Port Catheter Drug Pump Delivery System DPCDPD 100 has two points of entry into the spine of the patient with the Dual port catheter having a middle portion 112 secured in the epidural space, the proximal end 119 and distal end 114 outside the patient's body. The vertebrae (V1, V2, V3, V4, V5 and V6) may represent any six or more consecutive vertebrae of the spine. The Dual Port Catheter Drug Pump Delivery System DPCDPD 100 may have two positions that exit the spinal canal, a proximal end 119 and a distal end 114 leaving a middle portion 112 firmly secured in the epidural space of the spine. The Dual Port Catheter Drug Pump Delivery System DPCDPD 100 may be any length in size. The Dual Port Catheter Drug Pump Delivery System DPCDPD 100 may be utilized in the cervical region of the spine, thoracic region of the spine, lumbar region of the spine, and/or sacral region of the spine. The Dual Port Catheter Drug Pump Delivery System DPCDPD 100 may be placed anywhere along the spine within the epidural space or subdural space traversing one or more levels of the spine.

Having a two pump system 117c, 117d may be advantageous in the event of malfunction of one pump or if the catheter line becomes blocked not allowing medicine to flow freely. If the proximal drug pump unit 117c, is the main pump, and malfunctions or becomes clogged the distal drug pump unit 117d will be alerted and take over main pump duties to prevent a dangerous fall in medication concentration. As depicted in FIG. 14, the pores or apertures 111 that are represented by eleven circle like figures are where the medicines will be distributed from into the epidural space. In this depiction, the distal end 114 of the Dual Port Catheter Drug Pump Delivery System DPCDPD 100 exits the spinal cord between V1 and V2 through at the exit point 110. The proximal end of the Dual Port Catheter Drug Pump Delivery System DPCDPD 100 enters the spinal cord between V4 and V5 through the entrance point 118. The middle portion 112 of the Dual Port Catheter Drug Pump Delivery System DPCDPD 100 may be entered into the epidural space of the spinal cord by percutaneous epidural needles using T-Technique. The middle portion 112 of the Dual Port Catheter Drug Pump Delivery System DPCDPD may be controlled outside the patient's body by a practitioner by manipulating the distal end 114 and/or the proximal end 119 as previously discussed.

The percutaneous technique and the system deployed therein by plurality of embodiments described may also be adapted for use in the periphery of the body. To be clear, although the exemplary embodiments disclosed above pertain to deployment within an epidural space, the stimulators and pain pumps herein described may also be used outside the epidural space. In this embodiment, percutaneous access may be gained as previously disclosed, but the stimulator and/or pain pump may be advanced in through skin through needle and placed into place along muscle, fat, nerve, or bone, as desired with other end coming out of skin forming a loop and/or connection in the body.

While the disclosed technology has been related in terms of the foregoing embodiments, those skilled in the art will recognize that the invention may be not limited to the embodiments described. The present invention may be practiced with modification and alteration within the spirit and scope of the appended claims. Thus, the description is to be regarded as illustrative instead of restrictive on the present invention.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The invention claimed is:

1. A dual input and dual source spinal cord stimulator lead, comprising:
   a proximal portion that is configured for placement external to an epidural space through a first opening in a patient, wherein said proximal portion is configured for being accessed external to the epidural space and operatively connected to a first IPG unit;
   a distal portion that is configured for placement external to the epidural space through a second opening in the patient, wherein said distal portion is configured for being accessed external to the epidural space and operatively connected to a second IPG unit; and
   a middle portion between the proximal and distal portions that is configured for percutaneous placement in the epidural space,
   wherein said middle portion includes at least one stimulator electrode for placement completely inside the patient adjacent to target dura, and
   wherein said middle portion is controllable from outside the patient by manipulating the proximal or distal portions.

2. The spinal cord stimulator lead according to claim 1, wherein said proximal portion is coupled with a guide wire, a device or a medical tool.

3. The spinal cord stimulator lead according to claim 2, wherein said distal portion is coupled to a guide wire, a device or a medical tool.

4. The spinal cord stimulator lead according to claim 1, wherein said distal portion is anchored outside of the epidural space.

5. The spinal cord stimulator lead according to claim 1, wherein said middle portion further comprises a stimulator paddle traversable along said middle portion, said stimulator paddle being externally controllable.

6. The spinal cord stimulator lead according to claim 1, wherein said middle portion is capable of being folded or rolled up upon itself and once inside the epidural space is expandable.

7. The spinal cord stimulator lead according to claim 1, further comprising a wireless interface that is configured to communicate with an application configured to monitor and manipulate the electrical parameters of said at least one electrode.

8. A dual input and dual source spinal cord stimulator lead, comprising:
   a proximal portion that is configured for placement external to an epidural space through a first opening in a patient, wherein said proximal portion is operatively connected to a first IPG unit;
   a distal portion that is configured for placement external to the epidural space through a second opening in the patient, wherein said distal portion is operatively connected to a second IPG unit; and
   a middle portion between the proximal and distal portions that is configured for percutaneous placement in the epidural space,
   wherein said middle portion includes at least one stimulator electrode for placement completely inside the patient adjacent to target dura,
   wherein said middle portion is controllable from outside the patient by manipulating the proximal and/or distal portions having at least one electrode that is configured to expand and contract to facilitate placement and removal.

9. The spinal cord stimulator lead according to claim 1, further comprising a plurality of porous lumens that are configured to deliver medicine, gas, powder, or liquid to the target dura and epidural space.

* * * * *